(12) United States Patent
Pankratz et al.

(10) Patent No.: US 9,927,341 B2
(45) Date of Patent: Mar. 27, 2018

(54) VIBRATING MEMBER FOR A VIBRATING DENSITOMETER

(71) Applicant: Micro Motion, Inc., Boulder, CO (US)

(72) Inventors: Anthony William Pankratz, Arvada, CO (US); Megan Casey, Boulder, CO (US)

(73) Assignee: Micro Motion, Inc., Boulder, CO (US)

( * ) Notice: Subject to any disclaimer, the term of this patent is extended or adjusted under 35 U.S.C. 154(b) by 312 days.

(21) Appl. No.: 14/778,185

(22) PCT Filed: Apr. 4, 2013

(86) PCT No.: PCT/US2013/035298
§ 371 (c)(1),
(2) Date: Sep. 18, 2015

(87) PCT Pub. No.: WO2014/163642
PCT Pub. Date: Oct. 9, 2014

(65) Prior Publication Data
US 2016/0097703 A1    Apr. 7, 2016

(51) Int. Cl.
*G01N 9/00* (2006.01)
*G01N 29/036* (2006.01)
*G01N 29/22* (2006.01)

(52) U.S. Cl.
CPC ........... *G01N 9/002* (2013.01); *G01N 29/036* (2013.01); *G01N 29/222* (2013.01); *G01N 2009/006* (2013.01); *G01N 2291/02818* (2013.01)

(58) Field of Classification Search
USPC ......................................................... 73/32 A
See application file for complete search history.

(56) References Cited

U.S. PATENT DOCUMENTS

| | | | | |
|---|---|---|---|---|
| 3,874,221 A | * | 4/1975 | Lockie | G01L 9/0008 374/117 |
| 4,262,523 A | | 4/1981 | Stansfeld | |
| 4,429,564 A | | 2/1984 | Ikeda et al. | |
| 4,495,818 A | | 1/1985 | Ikeda et al. | |
| 4,683,752 A | * | 8/1987 | Bradshaw | G01H 5/00 73/290 V |

(Continued)

FOREIGN PATENT DOCUMENTS

| | | |
|---|---|---|
| DE | 3215040 A1 | 11/1983 |
| DE | 4034883 A1 | 5/1992 |

(Continued)

*Primary Examiner* — Paul West
*Assistant Examiner* — Mark A Shabman
(74) *Attorney, Agent, or Firm* — The Ollila Law Group LLC

(57) ABSTRACT

A vibrating member (412) adapted for use in a vibrating densitometer (400) includes a base (407) and a vibrating tube portion (405) affixed to the base (407). The vibrating tube portion (405) includes a first arcuate portion (430a), a second arcuate portion (430b), a first non-arcuate portion (432a), and a second non-arcuate portion (432b). The first and second non-arcuate portions (432a, 432b) are located between the first and second arcuate portions (430a, 430b). The vibrating tube portion (405) is formed with an oblong cross-sectional shape having a major axis dimension that is greater than a minor axis dimension. The oblong cross-sectional shape increases a frequency separation between vibration modes in the vibrating tube portion (405).

16 Claims, 5 Drawing Sheets

(56) References Cited

U.S. PATENT DOCUMENTS

| | | | |
|---|---|---|---|
| 5,373,745 A | 12/1994 | Cage | |
| 6,029,501 A * | 2/2000 | Nishino | G01N 9/002 |
| | | | 73/32 A |
| 8,590,400 B2 * | 11/2013 | Keita | G01F 1/8495 |
| | | | 73/861.355 |
| 2013/0133418 A1 * | 5/2013 | Van Cleve | G01N 9/002 |
| | | | 73/32 A |

FOREIGN PATENT DOCUMENTS

| | | |
|---|---|---|
| WO | 2011018312 A1 | 2/2011 |
| WO | 2012030353 A2 | 3/2012 |
| WO | WO 2012030353 A2 * 3/2012 | ............. G01N 9/002 |

* cited by examiner

US 9,927,341 B2

VIBRATING MEMBER FOR A VIBRATING DENSITOMETER

BACKGROUND OF THE INVENTION

1. Field of the Invention

The present invention relates to a vibrating densitometer, and more particularly, to a vibrating member of a vibrating densitometer.

2. Statement of the Problem

Densitometers are generally known in the art and are used to measure a density of a fluid. The fluid may comprise a liquid, a gas, a liquid with suspended particulates and/or entrained gas, or a combination thereof.

Vibrating densitometers can comprise a vibrating member, such as a cylinder that is exposed to a fluid under test. One example of a vibrating densitometer comprises a cylindrical conduit that is cantilever-mounted, with an inlet end coupled to an existing pipeline or other structure and with the outlet end free to vibrate. The conduit can be vibrated and a resonant frequency can be measured. As is generally known in the art, the density of the fluid under test can be determined by measuring a resonant frequency of the conduit in the presence of a flow fluid. According to well-known principles, the resonant frequency of the conduit will vary inversely with the density of the fluid that is contacting the conduit.

FIG. 1 shows a prior art vibrating cylinder of a vibrating gas densitometer. Such vibrating cylinder elements are useful in determining the density of gases, since gases have low densities. The prior art round vibrating cylinder may be vibrated at or near to a natural (i.e., resonant) frequency. By measuring a resonant frequency of the cylinder in a presence of a gas, the density of the gas can be determined. The prior art vibrating cylinder may be formed of metal and is desirably of a uniform thickness so that variations and/or imperfections in the cylinder wall do not affect the resonant frequency of the vibrating cylinder.

In theory, a cylinder having a perfectly round and uniform cross-sectional shape will result in only one three-lobed frequency mode shape. However, real world asymmetries caused by tolerance differences and other irregularities or imperfections will result in a supposedly circular tube producing two vibration mode shapes that are very close together in frequency (see FIG. 3). This is problematic, as it may be practically impossible to distinguish between the two vibration modes. As a result, the prior art vibrating densitometer may generate a resonant frequency value that is a mixture or combination of the two vibration modes, introducing error into the density measurement.

FIG. 2 shows a prior art densitometer. The prior art densitometer includes a cylindrical vibrating member located at least partially within a housing. The housing or the vibrating member may include flanges or other members for operatively coupling the densitometer to a pipeline or similar fluid delivering device in a fluid-tight manner. In the example shown, the vibrating member is cantilever mounted to the housing at an inlet end. The opposite end is free to vibrate. The vibrating member includes a plurality of fluid apertures that allow fluid to enter the densitometer and flow between the housing and the vibrating member. Therefore, the fluid contacts the inside as well as the outside surfaces of the vibrating member. This is particularly helpful when the fluid under test comprises a gas, as a greater surface area is exposed to the gas. In other examples, apertures may be provided in the housing and the vibrating member apertures may not be required.

A driver and a vibration sensor are positioned within a cylinder. The driver receives a drive signal from a meter electronics and vibrates the vibrating member at or near a resonant frequency. The vibration sensor detects the vibration of the vibrating member and sends the vibration information to the meter electronics for processing. The meter electronics determines the resonant frequency of the vibrating member and generates a density measurement from the measured resonant frequency.

To obtain accurate density measurements, the resonant frequency must be very stable. One prior art approach to achieve the desired stability is to vibrate the vibrating member in a radial vibration mode. In a radial vibration mode, the longitudinal axis of the vibrating member remains essentially stationary while at least a part of the vibrating member's wall translates and/or rotates away from its rest position. Radial vibration modes are preferred in straight conduit densitometers because radial vibration modes are self-balancing and thus, the mounting characteristics of the vibrating member are not as critical compared to some other vibration modes.

FIG. 3 shows the motion of a wall of a vibrating member exhibiting a first radial vibration mode and a second radial vibration mode. This is an example of a radial vibration mode that comprises a three-lobed radial vibration shape.

The key design criterion for a gas density cylinder is to separate the vibration mode shapes so that the mode shapes can be easily and accurately discriminated. If the vibrating member has a perfectly round cross-sectional shape and has a perfectly uniform wall thickness, there is only one three-lobed radial vibration mode. However, due to design tolerances, this is usually not achievable. Consequently, when a manufacturer attempts to make a perfectly round vibrating member with a perfectly uniform wall thickness, small imperfections result in two three-lobed radial vibrations that vibrate at two vibration modes that are very close to one another in frequency. The frequency separation between the two modes is typically very small and may be less than one Hertz, for example. With the two frequencies close together, a density determination may be difficult or impossible.

In some prior art densitometers, this problem is addressed by tuning the vibrating member so that it possesses a minimum frequency separation between the radial vibration modes. The tuning can be accomplished according to a variety of techniques, including forming lengthwise thicker and thinner regions in the vibrating member's wall in axially aligned strips. However, this prior art thickness tuning still requires extremely tight tolerances and results in manufacturing difficulties and high costs.

Therefore, there exists a need for a vibrating densitometer with increased vibration mode separation.

ASPECTS OF THE INVENTION

In one aspect of the invention, a vibrating member for use in a vibrating densitometer comprises:
  a base; and
  a vibrating tube portion affixed to the base, with the vibrating tube portion comprising:
    a first arcuate portion;
    a second arcuate portion;
    a first non-arcuate portion; and
    a second non-arcuate portion, with the first and second non-arcuate portions being located between the first and second arcuate portions, wherein the vibrating tube portion is formed with an oblong cross-sectional shape having a major axis dimension that is greater than a minor axis dimension and wherein the oblong cross-sectional shape increases a frequency separation between vibration modes in the vibrating tube portion.

Preferably, the vibrating tube portion is configured to be vibrated in one or more radial vibration modes.

Preferably, the first and second non-arcuate portions provide an offset span (OS) between the first and second arcuate portions.

Preferably, the first and second non-arcuate portions provide an offset span (OS) between the first and second arcuate portions, wherein an increase in the offset span (OS) increases a frequency separation between a first radial vibration mode and a second radial vibration mode.

Preferably, the first and second non-arcuate portions are affixed to the first and second arcuate portions.

Preferably, the first and second non-arcuate portions are welded or brazed to the first and second arcuate portions.

Preferably, the first and second non-arcuate portions extend a length of the vibrating tube portion.

Preferably, the vibrating tube portion is included in a housing of a vibrating densitometer.

Preferably, the vibrating densitometer includes a driver configured to vibrate the vibrating tube portion with respect to the housing and including at least one vibration sensor.

In one aspect of the invention, a method for forming a vibrating member for use in a vibrating densitometer comprises:
  forming a base;
  forming a vibrating tube portion comprising a first arcuate portion, a second arcuate portion, a first non-arcuate portion, and a second non-arcuate portion, with the first and second non-arcuate portions being located between the first arcuate portion and the second arcuate portion, wherein the vibrating tube portion is formed with an oblong cross-sectional shape having a major axis dimension that is greater than a minor axis dimension and wherein the oblong cross-sectional shape increases a frequency separation between vibration modes in the vibrating tube portion; and
  affixing the vibrating tube portion to the base.

Preferably, the vibrating tube portion is configured to be vibrated in one or more radial vibration modes.

Preferably, the first and second non-arcuate portions provide an offset span (OS) between the first and second arcuate portions.

Preferably, the first and second non-arcuate portions provide an offset span (OS) between the first and second arcuate portions, wherein an increase in the offset span (OS) increases a frequency separation between a first radial vibration mode and a second radial vibration mode.

Preferably, forming the vibrating tube portion further comprises affixing the first and second non-arcuate portions to the first and second arcuate portions.

Preferably, forming the vibrating tube portion further comprises welding or brazing the first and second non-arcuate portions to the first and second arcuate portions.

Preferably, forming the first and second non-arcuate portions further comprises forming the first and second non-arcuate portions to extend a length of the vibrating tube portion.

Preferably, the method further comprises a step of coupling an inlet end of the vibrating tube portion to a housing of a vibrating densitometer such that at least a portion of the vibrating tube portion is located within the housing.

Preferably, the method further comprises providing a driver positioned to vibrate the vibrating tube portion and providing at least one vibration sensor positioned to quantify vibrations of the vibrating tube portion.

DESCRIPTION OF THE DRAWINGS

The same reference number represents the same element on all drawings. The drawings are not necessarily to scale.

DETAILED DESCRIPTION OF THE INVENTION

FIGS. 4-7 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 4:
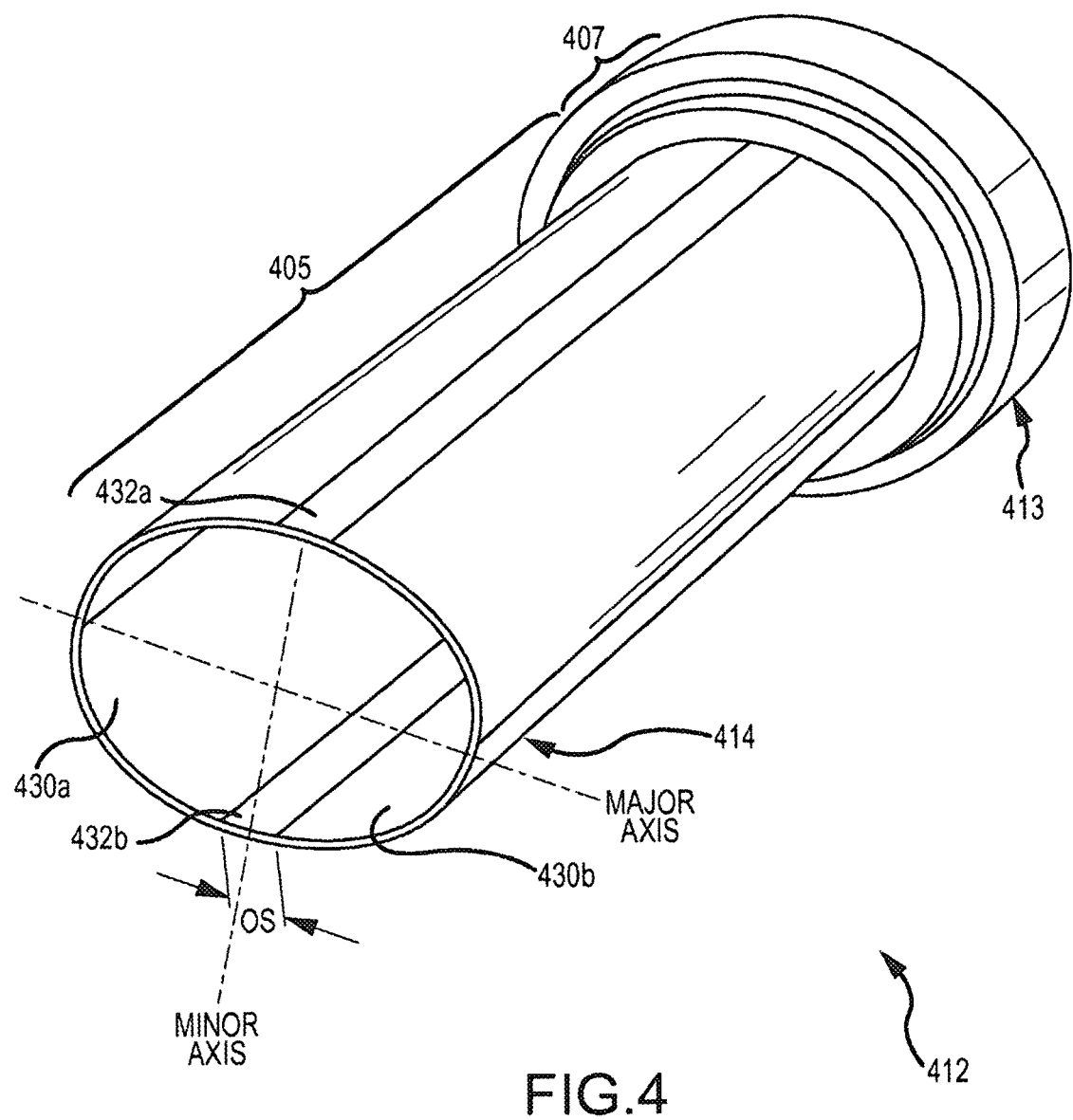
FIG. 4 shows a vibrating member for use in a vibrating densitometer according to an embodiment of the invention.

FIG. 4 shows a vibrating member 412 for use in a vibrating densitometer 400 according to an embodiment of the invention. The vibrating member 412 in the embodiment shown includes a base 407 and an elongated vibrating tube portion 405 affixed to the base 407. The vibrating member 412 is substantially hollow and includes an inlet end 413 and an outlet end 414. The base 407 is located at the inlet end 413 of the vibrating member 412. The inlet end 413 may be coupled to a housing 401 or other component of the vibrating densitometer 400 (see FIG. 5). Fluid entering or passing through the vibrating member 412 enters at the inlet end 413 and may exit at the outlet end 414.

Figure 1:
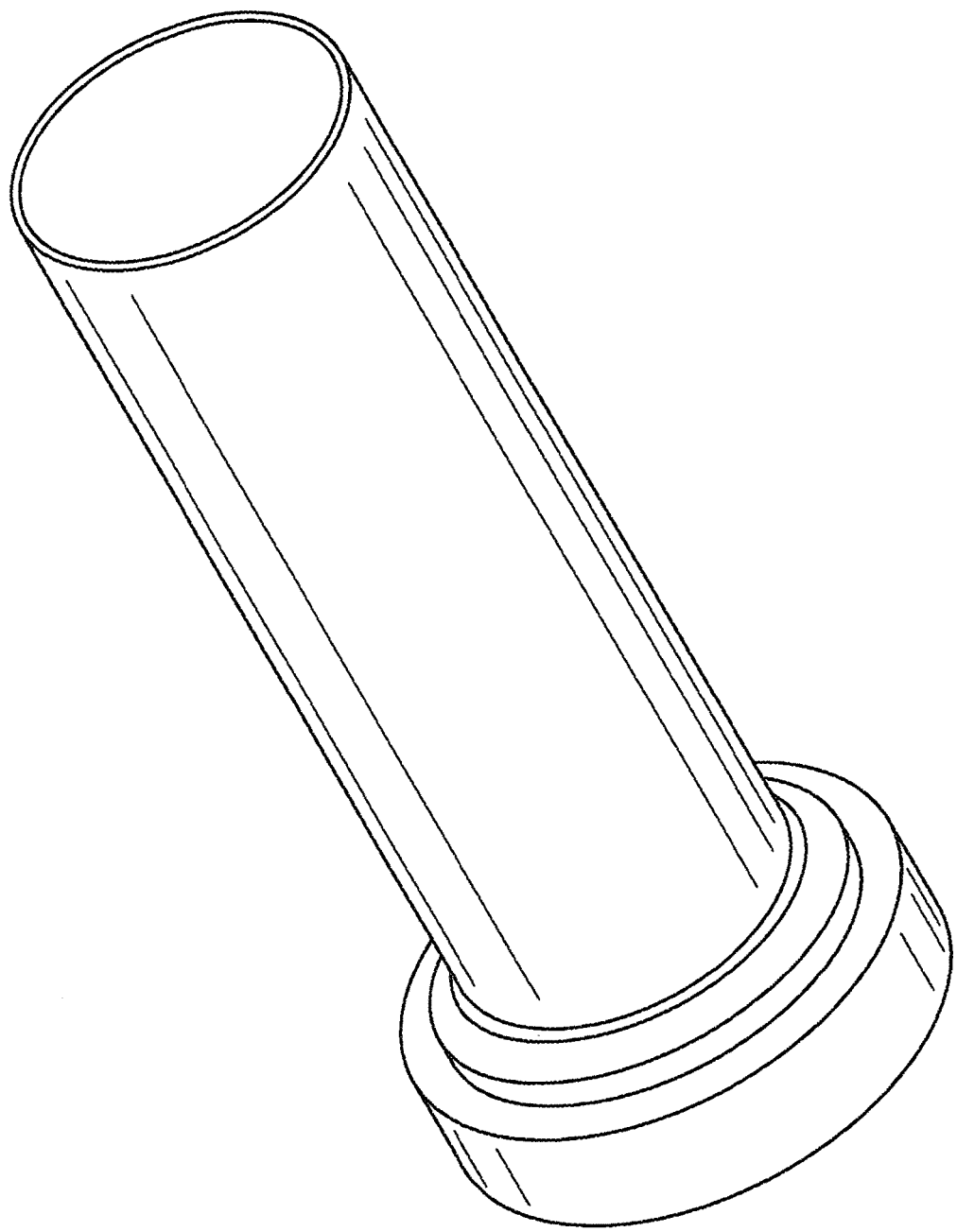
FIG. 1 shows a prior art vibrating cylinder of a vibrating gas densitometer.
Figure 2:
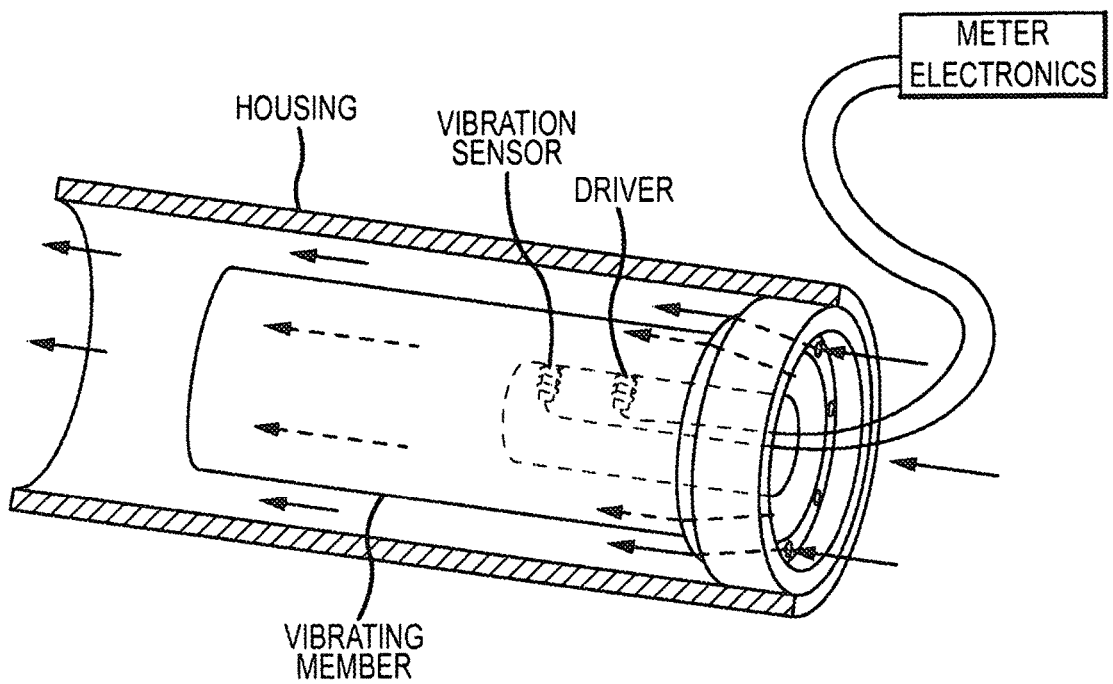
FIG. 2 shows a prior art densitometer.
Figure 3:
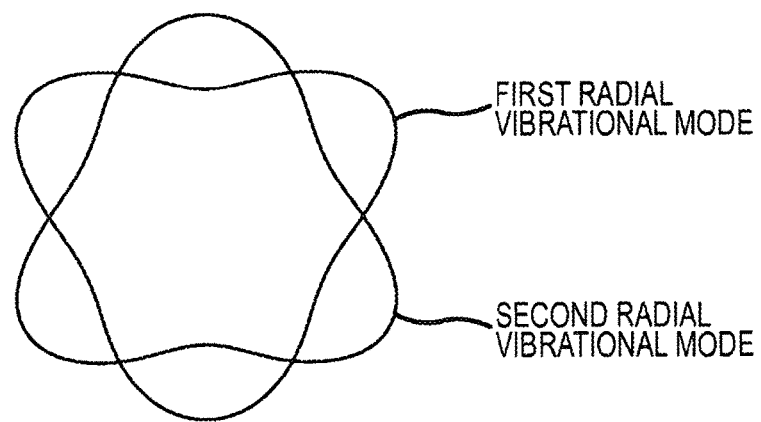
FIG. 3 shows the motion of a wall of a vibrating member exhibiting a first radial vibration mode and a second radial vibration mode.

The vibrating tube portion 405 comprises the density-sensing element. The vibrating tube portion 405 may comprise a thin metal tube in some embodiments. In operation, the vibrating tube portion 405 is activated so that it vibrates in a radial mode at its natural frequency (see FIG. 3, for example). The vibrating member 412 (and therefore the vibrating tube portion 405) is configured to be vibrated in one or more radial vibration modes. The gas is passed over the outer and inner surfaces of the tube and therefore is in contact with the wall of the vibrating tube portion 405. The mass of gas, which vibrates with the tube, depends upon the gas density. Since increasing the vibrating mass decreases the natural frequency of vibration, the gas density is determined by measuring the natural or resonant vibration frequency of the vibrating member 412 when the vibrating member 412 is vibrated in the presence of a fluid.

The vibrating tube portion 405 comprises a tube including a first arcuate portion 430a, a second arcuate portion 430b, a first non-arcuate portion 432a, and a second non-arcuate portion 432b. The first and second non-arcuate portions 432a and 432b are located between the first arcuate portion 430a and the second arcuate portion 430b. The two non-arcuate portions 432a and 432b are located in diametrically opposite sides of the vibrating tube portion 405 and space apart the first arcuate portion 430a and the second arcuate portion 430b. The two non-arcuate portions 432a and 432b have a size that creates an offset span OS in the vibrating tube portion 405. An increase in the offset span OS will correspondingly increase the dimension of the major axis, while the minor axis may be defined by the diameter of the first and second arcuate portions 430a and 430b.

The two non-arcuate portions 432a and 432b are substantially planar in the embodiment shown. Alternatively, the two non-arcuate portions 432a and 432b may have other shapes. In some embodiments, the first and second non-arcuate portions 432a and 432b extend substantially a length of the vibrating tube portion 405.

The offset span OS can be chosen to comprise any desired span. However, it should be understood that as the offset span OS is increased, a frequency separation correspondingly increases. The frequency separation comprises a frequency separation between vibration modes, such as radial vibration modes. For example, the frequency separation can comprise a frequency separation between a first radial vibration mode and a second radial vibration mode. As a result, the frequency separation between the first vibration mode and the second vibration mode can be chosen by the designer of the vibrating densitometer 400 by the appropriate selection of the offset span OS.

The two non-arcuate portions 432a and 432b create an oblong or elongated cross-sectional shape in the vibrating tube portion 405. The vibrating tube portion 405 is formed with an oblong shape having a major axis dimension that is greater than a minor axis dimension and wherein the oblong cross-sectional shape increases a frequency separation between the vibration modes in the vibrating tube portion 405.

The term "oblong" in the context of the invention means that the cross-sectional shape of the vibrating tube portion 405 is longer or wider in one dimension than in the other. Here, as is labeled in the figure, the horizontal axis comprises the major axis and the vertical axis comprises the minor axis, wherein the major axis dimension is greater than the minor axis dimension. The vibrating tube portion 405 comprises a substantially circular cross-section wherein the cross-sectional shape is made oblong by the inclusion of the two non-arcuate portions 432a and 432b. The vibrating tube portion 405 does not have a rectangular shape, however, and retains the smooth, uniform rounded portions A and B.

In some embodiments, the first and second arcuate portions 430a and 430b extend over about one-hundred and eighty degrees of arc. Alternatively, the first and second arcuate portions 430a and 430b may include more than or less than one-hundred eighty degrees of arc.

Advantageously, the long ends of an oblong cross-sectional structure will affect the modal shape in a predetermined direction, and thus separate the drive mode from the other interfering mode. Another benefit is that the flat sides of the oblong shape are less resistant to bending and are able to separate the frequencies better than a true oval or ellipse.

In some embodiments, the offset distance OD can be selected to provide the desired frequency separation. According to an embodiment, the frequency separation between the intended drive mode and unintended modes will equal or exceed a threshold amount. For example, some embodiments may require that the lower frequency three-lobed radial vibration mode is separated from the next closest vibration mode by at least 10 Hz. It should be appreciated however, that 10 Hz is merely one example and the particular frequency separation will vary from one application to another and should in no way limit the claims that follow.

In some embodiments, the oblong-shaped tube will require a tolerance of only about +/−0.001 inch. Because the wall thickness is not being used for controlling the vibration modes, the manufacture of the vibrating member 412 is simplified and the cost is reduced, as the frequency separation is not dependent on achieving very tight shape tolerances during manufacturing. In addition, some variation in wall thickness can be tolerated if the oblong cross-sectional shape sufficiently spaces apart the vibration modes of the vibrating member 412. The current invention uses the new and unique geometry of the oblong cross-sectional shape of the tube to separate the two frequencies, to improve design robustness, and to make the design less sensitive to manufacturing tolerances (manufacturing tolerance differences).

During construction of the elongated vibrating tube portion 405, a base 407 is formed. A vibrating tube portion 405 is also formed, with the vibrating tube portion 405 comprising first and second arcuate portions 430a and 430b and first and second non-arcuate portions 432a and 432b. The first and second non-arcuate portions 432a and 432b are positioned between the first and second arcuate portions 430a and 430b. The first and second non-arcuate portions 432a and 432b may be affixed to the first and second arcuate portions 430a and 430b, spacing apart the first and second arcuate portions 430a and 430b. In some embodiments, the first and second non-arcuate portions 432a and 432b may be welded to the first and second arcuate portions 430a and 430b. Alternatively, the first and second non-arcuate portions 432a and 432b may be brazed to the first and second arcuate portions 430a and 430b. However, it should be understood that welding and brazing are provided merely as examples, and other suitable affixing methods may be employed.

Alternatively, the oblong cross-sectional shape of the vibrating tube portion 405 may be formed in other ways. For example, the vibrating tube portion 405 may comprise a circular cross-section tube that is compressed and squashed into the oblong cross-sectional shape. In some embodiments, a mandrel or other component may be inserted into the vibrating tube portion 405 before it is compressed, wherein the vibrating tube portion 405 is compressed onto the inserted mandrel and the inserted mandrel ensures that a proper oblong cross-sectional shape is achieved.

In yet another alternative, the oblong cross-sectional shape can be formed by stretching (or heating and stretching) a round vibrating tube portion 405.

The vibrating tube portion 405 is subsequently affixed to the base 407. The vibrating tube portion 405 may be welded or brazed to the base 407 in some embodiments. However, it should be understood that the vibrating tube portion 405 may be affixed to the base 407 in any suitable manner, including being permanently or removably affixed to the base 407.

In operation, the wall of the vibrating tube portion 405 is excited in a radial direction and in a radial vibration mode by a driver or other excitation mechanism. The wall of the elongated vibrating tube portion 405 will then vibrate in a corresponding radial mode, but at a resonant frequency of the elongated vibrating tube portion 405 and the surrounding flow fluid. The relationship between the driving force of the vibration and the asymmetry of the tube wall will cause one or both of the mode shapes to be excited.

The oblong vibrating tube portion 405 separates the resulting vibration modes by at least a predetermined frequency difference, making discrimination between the vibration modes both practical and easier to achieve. Consequently, the vibrating densitometer 400 can filter or otherwise separate or discriminate the vibration modes picked up by the at least one vibration sensor 417. For example, the oblong vibrating tube portion 405 can separate and space apart a lower frequency radial vibration mode from a higher frequency radial vibration mode.

Although the discussion herein concerns a vibrating tube that is fixed at one end and free at the other end, it should be understood that the concepts and examples also apply to a tube that is fixed at both ends and is vibrated in a radial mode.

Figure 5:
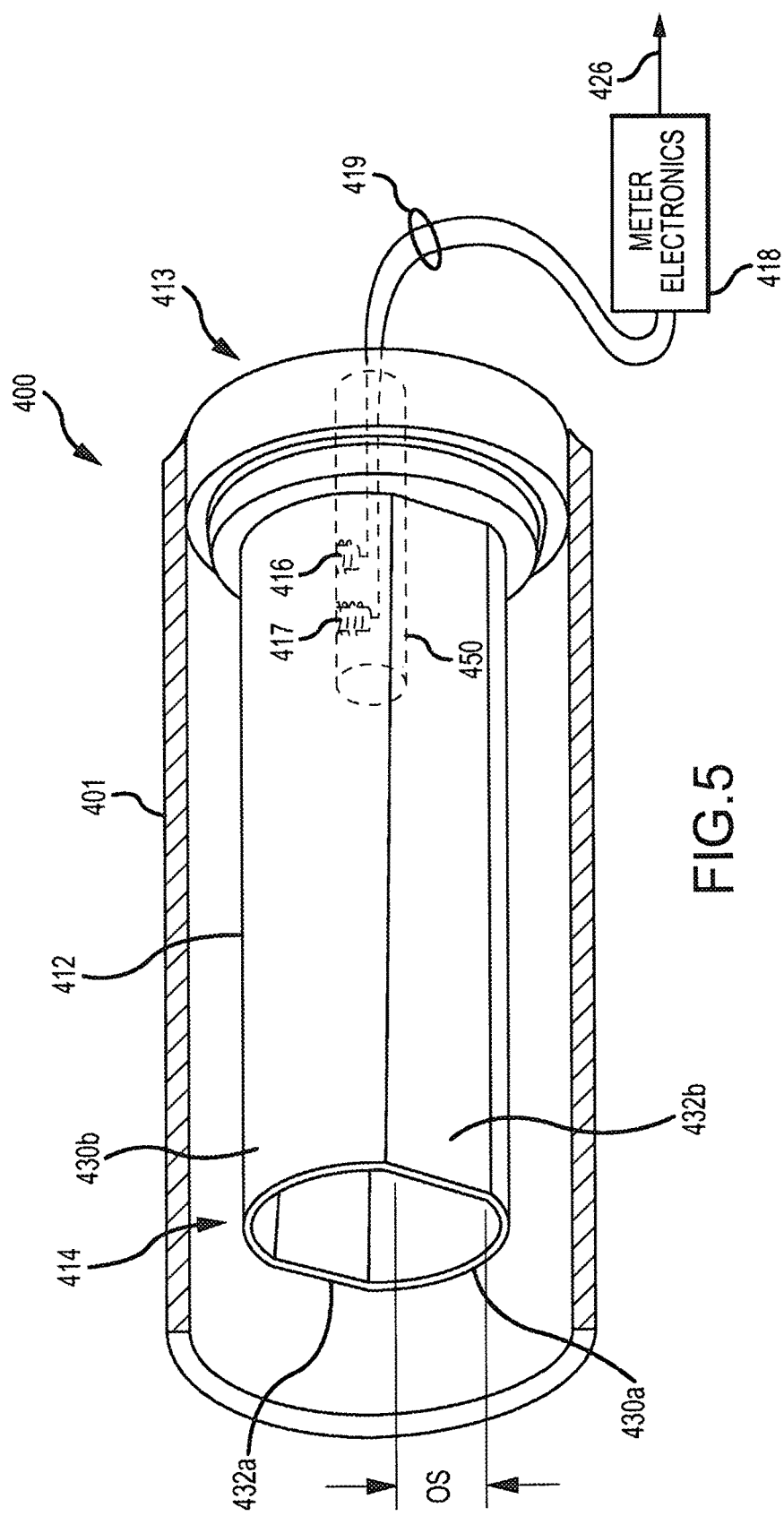
FIG. 5 shows a vibrating densitometer according to an embodiment.

FIG. 5 shows a vibrating densitometer 400 according to an embodiment. The vibrating densitometer 400 may be configured to determine a density of a fluid, such as a gas, a liquid, a liquid with entrained gas, a liquid with suspended particulates, or a combination thereof. Due to viscous damping, the vibrating densitometer 400 is typically used to measure a density of a gas rather than a density of a liquid.

According to an embodiment, the vibrating densitometer 400 includes the vibrating member 412 inside a housing 401. The vibrating member 412 may be permanently or removably affixed to the housing 401. The fluid to be quantified may be introduced into or may be passed through the housing 401. The vibrating member 412 may be substantially coaxial within the housing 401 in some embodiments. However, the vibrating member 412 does not completely correspond to the housing 401 in cross-sectional shape.

When the vibrating tube portion 405 is installed in the vibrating densitometer 400, the inlet end 413 of the vibrating member 412 is coupled to the housing 401 while the outlet end 414 is free to vibrate. The vibrating tube portion 405 is not directly coupled to the housing 401 in the embodiment shown, wherein the base 407 is coupled to the housing 401 and the outlet end 414 is free to vibrate. As a result, the vibrating tube portion 405 is cantilever-mounted to the housing 401.

According to an embodiment, the vibrating densitometer 400 can further include a driver 416 and at least one vibration sensor 417, which can be coupled to a central tower or body 450. The driver 416 can be adapted to vibrate the vibrating member 400 in one or more vibration modes. While the driver 416 is shown located within a central tower 450 positioned within the vibrating member 412, in some embodiments the driver 416 may be positioned between the housing 401 and the vibrating member 412, for example. Furthermore, it should be appreciated that while the driver 416 is shown positioned closer to the inlet end 413, the driver 416 may be positioned at any desired location. According to an embodiment, the driver 416 can receive an electrical signal from the meter electronics 418 via leads 419. According to one embodiment, the driver 416 can be located or centered on one of the arcuate portions 430a or 430b, for example. Alternatively, the driver 416 can be located or centered on one of the non-arcuate portions 432a or 432b.

In the embodiment shown, the at least one vibration sensor 417 is coaxially aligned with the driver 416. In other embodiments, the at least one vibration sensor 417 may be coupled to the vibrating member 412 in other locations. For example, the at least one vibration sensor 417 may be located on an outer surface of the vibrating member 412. Further, the at least one vibration sensor 417 may be located outside the vibrating member 412 while the driver 416 is located inside the vibrating member 412, or vice versa.

The at least one vibration sensor 417 can transmit a signal to the meter electronics 418 via leads 419. The meter electronics 418 can process the signals received by the at least one vibration sensor 417 to determine a resonant frequency of the vibrating member 412. If a fluid under test is present, the resonant frequency of the vibrating member 400 will change inversely proportional to the fluid density as is known in the art. The proportional change may be determined during an initial calibration, for example. In the embodiment shown, the at least one vibration sensor 417 also comprises a coil. The driver 416 receives a current to induce a vibration in the vibrating member 412 and the at least one vibration sensor 417 uses the motion of the vibrating member 412 created by the driver 416 to induce a voltage. Coil drivers and sensors are well known in the art and a further discussion of their operation is omitted for brevity of the description. Furthermore, it should be appreciated that the driver 416 and the at least one vibration sensor 417 are not limited to coils, but rather may comprise a variety of other well-known vibrating components, such as piezo-electric sensors, for example. Therefore, the present embodiment should in no way be limited to coils. Furthermore, those skilled in the art will readily recognize that the particular placement of the driver 416 and the at least one vibration sensor 417 can be altered while remaining within the scope of the present embodiment.

The meter electronics 418 may be coupled to a bus 426 or other communication link. The meter electronics 418 may communicate density measurements over the bus 426. In addition, the meter electronics 418 may transmit any manner of other signals, measurements, or data over the bus 426. In addition, the meter electronics 418 may receive instructions, programming, or other data or commands via the bus 426.

Figure 6:
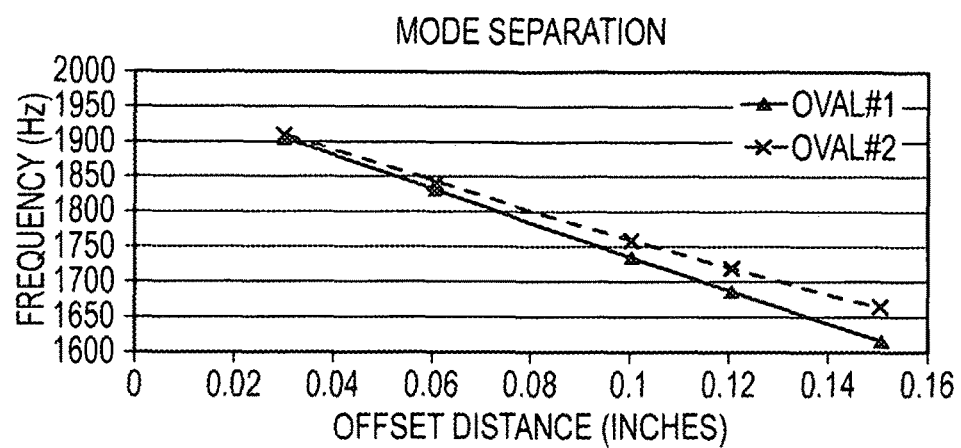
FIG. 6 is a graph of frequency versus an offset span OS, illustrating the effect of increasing offset span OS on frequency separation between first and second radial vibration modes in the vibrating densitometer.

FIG. 6 is a graph of frequency versus the offset span OS, illustrating the effect of increasing offset span OS on frequency separation between first and second radial vibration modes in the vibrating densitometer 400. The figure shows that as the offset span OS increases, the frequency separation correspondingly increases. The selected and/or increased frequency separation can produce a better performing sensor, wherein the vibration modes are easier to discriminate from each other.

Figure 7:
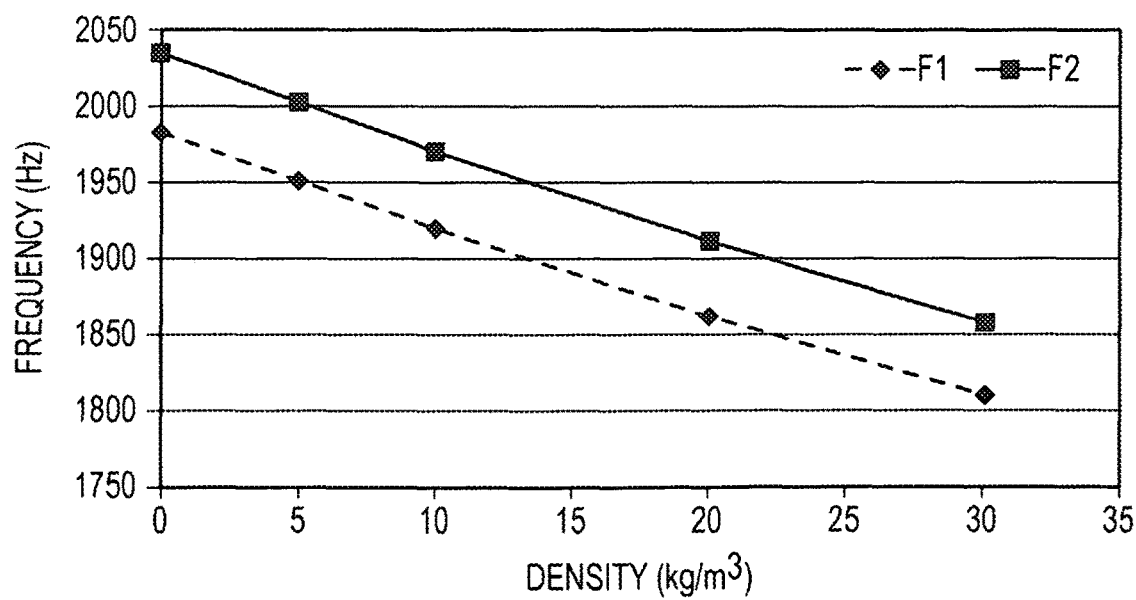
FIG. 7 is a graph of vibration frequency versus flow material density for the vibrating densitometer.

FIG. 7 is a graph of vibration frequency versus flow material density (in units of $kg/m^3$) for the vibrating densitometer 400. The graph shows the resonant frequency of the oblong-shaped vibrating tube portion 405 over a range of gas densities. The frequency/density relationship for the oblong tube follows the calibration curve of an actual vibrating tube portion. It can be seen from the graph that the frequency separation between the two vibration modes is also maintained across changing densities.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments are described herein for illustrative purposes, various equivalent modifications are possible within the scope of the present description, as those skilled in the relevant art will recognize. The teachings provided herein can be applied to other vibrating members, and not just to the embodiments described above and shown in the accompanying figures. Accordingly, the scope of the embodiments described above should be determined from the following claims.

What is claimed is:

1. A vibrating member (412) adapted for use in a vibrating densitometer (400), with the vibrating member (412) comprising:
   a base (407); and
   a vibrating tube portion (405) affixed to the base (407), with the vibrating tube portion (405) comprising:
      a first arcuate portion (430a);
      a second arcuate portion (430b);
      a first non-arcuate portion (432a); and
      a second non-arcuate portion (432b), with the first and second non-arcuate portions (432a, 432b) being located between the first and second arcuate portions (430a, 430b), wherein the vibrating tube portion (405) is formed with an oblong cross-sectional shape having a major axis dimension that is greater than a minor axis dimension and wherein the oblong cross-sectional shape increases a frequency separation between vibration modes in the vibrating tube portion (405), and wherein the first and second arcuate portions interface with respective first and second arcuate portions to define a plurality of respective axial edges.

2. The vibrating member (412) of claim 1, wherein the vibrating tube portion (405) is configured to be vibrated in one or more radial vibration modes.

3. The vibrating member (412) of claim 1, with the first and second non-arcuate portions (432a, 432b) providing an offset span (OS) between the first and second arcuate portions (430a, 430b).

4. The vibrating member (412) of claim 1, with the first and second non-arcuate portions (432a, 432b) being affixed to the first and second arcuate portions (430a, 430b).

5. The vibrating member (412) of claim 1, with the first and second non-arcuate portions (432a, 432b) being welded or brazed to the first and second arcuate portions (430a, 430b).

6. The vibrating member (412) of claim 1, wherein the first and second non-arcuate portions (432a, 432b) extend a length of the vibrating tube portion (405).

7. The vibrating member (412) of claim 1, wherein the vibrating tube portion (405) is included in a housing (401) of a vibrating densitometer (400).

8. The vibrating member (412) of claim 7, with the vibrating densitometer (400) including a driver (516) configured to vibrate the vibrating tube portion (412) with respect to the housing (401) and including at least one vibration sensor (417).

9. A method for forming a vibrating member adapted for use in a vibrating densitometer, with the method comprising:
   forming a base;
   forming a vibrating tube portion comprising a first arcuate portion, a second arcuate portion, a first non-arcuate portion, and a second non-arcuate portion, with the first and second non-arcuate portions being located between the first arcuate portion and the second arcuate portion, wherein the vibrating tube portion is formed with an oblong cross-sectional shape having a major axis dimension that is greater than a minor axis dimension and wherein the oblong cross-sectional shape increases a frequency separation between vibration modes in the vibrating tube portion, and wherein the first and second arcuate portions interface with respective first and second arcuate portions to define a plurality of respective axial edges; and
   affixing the vibrating tube portion to the base.

10. The method of claim 9, wherein the vibrating tube portion is configured to be vibrated in one or more radial vibration modes.

11. The method of claim 9, with the first and second non-arcuate portions providing an offset span (OS) between the first and second arcuate portions.

12. The method of claim 9, with forming the vibrating tube portion further comprising affixing the first and second non-arcuate portions to the first and second arcuate portions.

13. The method of claim 9, with forming the vibrating tube portion further comprising welding or brazing the first and second non-arcuate portions to the first and second arcuate portions.

14. The method of claim 9, with forming the first and second non-arcuate portions further comprising forming the first and second non-arcuate portions to extend a length of the vibrating tube portion.

15. The method of claim 9, further comprising a step of coupling an inlet end of the vibrating tube portion to a housing of a vibrating densitometer such that at least a portion of the vibrating tube portion is located within the housing.

16. The method of claim 15, further comprising:
   providing a driver positioned to vibrate the vibrating tube portion; and
   providing at least one vibration sensor positioned to quantify vibrations of the vibrating tube portion.

* * * * *